(12) United States Patent
Mentak et al.

(10) Patent No.: US 8,034,106 B2
(45) Date of Patent: Oct. 11, 2011

(54) INTERFACIAL REFRACTION ACCOMMODATING LENS (IRAL)

(75) Inventors: Khalid Mentak, San Ramon, CA (US); Beda Steinacher, Zurich (CH); Philipp Stücklin, Zurich (CH); Hans Flückiger, Oetwil am See (CH)

(73) Assignee: Adoptics AG, Port (CH)

( * ) Notice: Subject to any disclaimer, the term of this patent is extended or adjusted under 35 U.S.C. 154(b) by 167 days.

(21) Appl. No.: 12/388,254

(22) Filed: Feb. 18, 2009

(65) Prior Publication Data

US 2009/0264998 A1    Oct. 22, 2009

Related U.S. Application Data

(63) Continuation-in-part of application No. 12/025,512, filed on Feb. 4, 2008, now Pat. No. 7,857,850.

(60) Provisional application No. 60/887,933, filed on Feb. 2, 2007, provisional application No. 60/887,928, filed on Feb. 2, 2007.

(51) Int. Cl.
   *A61F 2/16*    (2006.01)
(52) U.S. Cl. .................. 623/6.13; 623/6.34; 623/6.37
(58) Field of Classification Search .................. 623/4.1, 623/6.11, 6.13
   See application file for complete search history.

(56) References Cited

U.S. PATENT DOCUMENTS

| | | |
|---|---|---|
| 4,037,929 A | 7/1977 | Bricot et al. |
| 4,056,855 A | 11/1977 | Kelman |
| 4,254,509 A | 3/1981 | Tennant |
| 4,564,267 A | 1/1986 | Nishimoto |
| 4,709,996 A | 12/1987 | Michelson |
| 4,720,286 A | 1/1988 | Bailey et al. |
| 4,729,641 A | 3/1988 | Matsuoka et al. |
| 4,781,440 A | 11/1988 | Akitoshi |
| 4,802,746 A | 2/1989 | Baba et al. |
| 4,816,031 A | 3/1989 | Pfoff |
| 4,890,903 A | 1/1990 | Treisman et al. |
| 4,932,966 A | 6/1990 | Christie et al. |
| 4,989,958 A | 2/1991 | Hamada et al. |
| 5,041,134 A | 8/1991 | O'Donnell |
| 5,443,506 A | 8/1995 | Garabet |

(Continued)

FOREIGN PATENT DOCUMENTS

EP        0162573 A2    11/1985

(Continued)

OTHER PUBLICATIONS

Supplementary European Search Report mailed on Dec. 10, 2009 for EP App. No. 08728944.3 filed on Aug. 2, 2009.

(Continued)

*Primary Examiner* — David H Willse
*Assistant Examiner* — Tiffany Shipmon
(74) *Attorney, Agent, or Firm* — Whyte Hirschboeck Dudek S.C.; Grady J. Frenchick

(57) ABSTRACT

This invention relates to intraocular lenses. More particularly, this invention relates to intraocular lenses that have the ability to alter the light refractive power in response to changes in the tension of the ciliary muscle or ciliary body of the eye or any other accommodative forces. Lenses of this invention are generally referred to as interfacial, i.e., lens properties being defined as the interface of two liquids having different refractive indices, refractive accommodating lenses (IRAL).

13 Claims, 21 Drawing Sheets

U.S. PATENT DOCUMENTS

| | | | |
|---|---|---|---|
| 5,489,302 A | 2/1996 | Skottun | |
| 5,493,427 A | 2/1996 | Nomura et al. | |
| 5,576,893 A | 11/1996 | Yamanouchi | |
| 6,081,388 A | 6/2000 | Widl | |
| 6,117,171 A * | 9/2000 | Skottun | 623/6.37 |
| 6,271,975 B1 | 8/2001 | Grupp | |
| 6,288,846 B1 | 9/2001 | Stoner, Jr. | |
| 6,299,641 B1 | 10/2001 | Woods | |
| 6,369,954 B1 | 4/2002 | Berge et al. | |
| 6,406,494 B1 | 6/2002 | Laguette et al. | |
| 6,449,081 B1 | 9/2002 | Onuki et al. | |
| 6,469,683 B1 | 10/2002 | Suyama et al. | |
| 6,485,516 B2 | 11/2002 | Boehm | |
| 6,488,708 B2 | 12/2002 | Sarfarazi | |
| 6,551,354 B1 | 4/2003 | Ghazizadeh et al. | |
| 6,558,420 B2 | 5/2003 | Green | |
| 6,730,123 B1 | 5/2004 | Klopotek | |
| 6,749,634 B2 | 6/2004 | Hanna | |
| 6,806,988 B2 | 10/2004 | Onuki et al. | |
| 6,855,164 B2 * | 2/2005 | Glazier | 623/6.37 |
| 6,859,333 B1 | 2/2005 | Ren et al. | |
| 6,864,951 B1 | 3/2005 | Ren et al. | |
| 6,882,482 B2 | 4/2005 | Ogasawara | |
| 6,950,219 B2 | 9/2005 | Onuki et al. | |
| 7,025,783 B2 | 4/2006 | Brady et al. | |
| 7,042,549 B1 | 5/2006 | Ren et al. | |
| 7,048,760 B2 | 5/2006 | Cumming | |
| 7,079,203 B1 | 7/2006 | Huang et al. | |
| 7,097,660 B2 | 8/2006 | Portney | |
| 7,125,422 B2 | 10/2006 | Woods et al. | |
| 7,126,903 B2 | 10/2006 | Feenstra et al. | |
| 7,142,344 B2 | 11/2006 | Onuki et al. | |
| 7,142,369 B2 | 11/2006 | Wu et al. | |
| 7,229,475 B2 | 6/2007 | Glazier | |
| 7,230,771 B2 | 6/2007 | Kuiper et al. | |
| 7,261,737 B2 | 8/2007 | Esch et al. | |
| 7,301,708 B2 | 11/2007 | Kuiper et al. | |
| 7,311,398 B2 | 12/2007 | Kuiper et al. | |
| 7,327,434 B1 | 2/2008 | Ren et al. | |
| 7,369,321 B1 | 5/2008 | Ren et al. | |
| 7,408,601 B1 | 8/2008 | Huang et al. | |
| 7,436,598 B2 | 10/2008 | Kuiper et al. | |
| 7,452,378 B2 | 11/2008 | Zadno-Azizi et al. | |
| 2001/0017985 A1 | 8/2001 | Tsuboi et al. | |
| 2004/0181279 A1 | 9/2004 | Nun | |
| 2006/0155372 A1 | 7/2006 | Coroneo | |
| 2006/0256429 A1 | 11/2006 | Obrebski et al. | |
| 2007/0021831 A1 | 1/2007 | Clarke | |
| 2007/0129799 A1 | 6/2007 | Schedler | |
| 2008/0188930 A1 | 8/2008 | Mentak | |

FOREIGN PATENT DOCUMENTS

| | | |
|---|---|---|
| WO | WO00/58763 | 10/2000 |
| WO | 02100300 A1 | 12/2002 |
| WO | WO2005096999 | 10/2005 |
| WO | WO2007107589 | 9/2007 |
| WO | WO2008070022 | 6/2008 |
| WO | WO2008097915 | 8/2008 |

OTHER PUBLICATIONS

European Examination Report mailed on Feb. 26, 2010 for EP App. No. 08728944.3 filed on Aug. 2, 2009.
International Search Report and Written Opinion mailed on Jul. 9, 2010 for PCT/US2010/024518 filed on Feb. 18, 2010.
Non-Final Office Action mailed Oct. 16, 2009, for U.S. Appl. No. 12/025,512, filed Feb. 4, 2008.
Final Office Action mailed Jun. 10, 2010, for U.S. Appl. No. 12/025,512, filed Feb. 4, 2008.
PCT International Search Report and Written Opinion for related PCT/US08/052933 (Feb. 4, 2008).
Bethke, Walter "A Sneak Peek into the IOL Pipeline," Review of Ophthalmology, Nov. 1, 2007; vol. No. 14:11.

* cited by examiner

ACCOMMODATED STATE

UNACCOMMODATED STATE

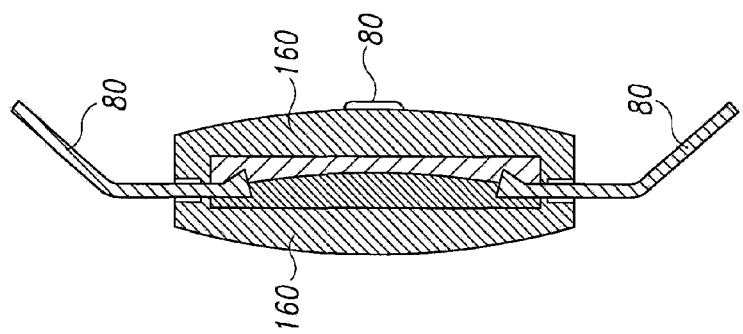
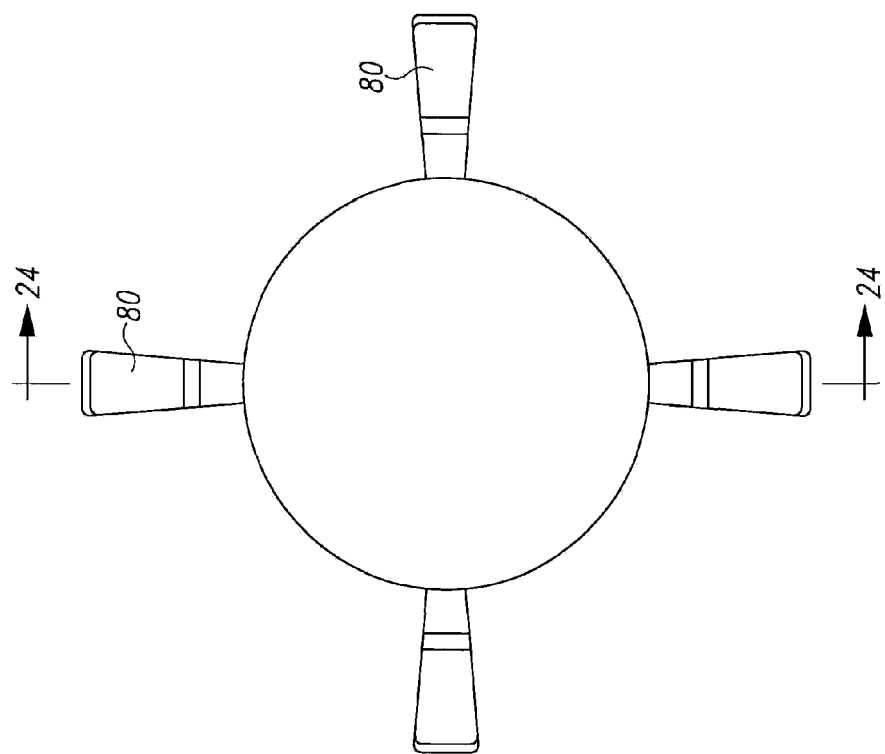
Fig. 24
Fig. 23

INTERFACIAL REFRACTION ACCOMMODATING LENS (IRAL)

CROSS REFERENCE TO RELATED APPLICATIONS

This application is a continuation-in-part of U.S. application Ser. No. 12/025,512 filed on Feb. 4, 2008 now U.S. Pat. No. 7,857,850 which claims the priority of U.S. provisional applications Ser. Nos. 60/887,933 and 60/887,928 both filed on Feb. 2, 2007, the disclosures of all of which are incorporated by reference herein (including any references incorporated by reference in either or both of said provisional applications) in their entireties.

FIELD OF THE INVENTION

This invention relates to intraocular lenses. More particularly, this invention relates to intraocular lenses that have the ability to alter the light refractive power in response to changes in the tension of the ciliary muscle or ciliary body of the eye or any other accommodative forces. Lenses of this invention are generally referred to as accommodating lenses.

BACKGROUND OF THE INVENTION

The natural lens of a human eye is a transparent crystalline body, which is contained within a capsular bag located behind the iris and in front of the vitreous cavity in a region known as the posterior chamber. The capsular bag is attached on all sides by fibers, called zonules, to a muscular ciliary body. At its rear, the vitreous cavity, which is filled with a gel further includes the retina, on which light rays passing through the lens are focused. Contraction and relaxation of the ciliary body changes the shape of the bag and of the natural lens therein, thereby enabling the eye to focus light rays originating from objects at various distances on the retina.

Cataracts occur when the natural lens of the eye or of its surrounding transparent membrane becomes clouded and obstructs the passage of light resulting in varying degrees of vision impairment. To correct this condition in a patient, a surgical procedure is performed in which the clouded natural lens, or cataract, is extracted and replaced by an artificial intraocular lens. During cataract surgery, the anterior portion of the capsular bag is removed along with the cataract, and the posterior portion of the capsular bag, called the posterior capsule, is sometimes left intact to serve as a support site for implanting the intraocular lens (IOL). Such conventional IOLs, however, have the drawback that they have a fixed refractive power and are therefore unable to change their focus in response to changing focal distance needs of the patient, such as reading, or working on a computer.

Various types of intraocular lenses having the capability of altering their refractive power have been suggested in an effort to duplicate the performance of the natural lens within the eye. Such accommodating intraocular lenses, as they are known in the art, have a variety of designs directed to enable the patient to focus on, and thereby clearly see, objects located at a plurality of distances. Examples may be found in such publications as U.S. Pat. Nos. 4,254,509; 4,932,966; 6,299,641; 6,406,494, and 7,261,737.

U.S. Pat. No. 5,443,506 to Garabet discloses a variable focus intraocular lens which alters the medium between the two surfaces of the lens to alter its accommodation. The lens of the '506 patent has continuous flow loops which couple a channel in first portion of the intraocular lens. The continuous flow loops, in addition to providing a channel, provide the means by which the intraocular lens is positioned and held in the eye. In one embodiment, the continuous flow loop(s) comprise the lens haptics i.e., the lens body supporting structures, which, in turn move a charged solution into an optical zone between solid lens surfaces to change the lens focus.

U.S. Pat. No. 5,489,302 discloses an accommodating intraocular lens for implantation in the posterior chamber of the eye. This lens comprises a short tubular rigid frame and transparent and resilient membrane attached thereto at its bases. The frame and the membranes confine a sealed space filled with a gas. The frame includes flexible regions attached via haptics to the posterior capsule. Upon stretching of the capsule by the eye's ciliary muscles, the flexible regions are pulled apart, thereby increasing the volume and decreasing the pressure within the sealed space. This changes the curvature of the membranes and accordingly, the refractive power of the lens.

U.S. Pat. No. 6,117,171 discloses an accommodating intraocular lens which is contained inside an encapsulating rigid shell so as to make it substantially insensitive to changes in the intraocular environment. The lens is adapted to be implanted within the posterior capsule and comprises a flexible transparent membrane, which divides the interior of the intraocular lens into separate front and rear spaces, each filled with a fluid having a different refractive index. The periphery of the rear space is attached to haptics, which are in turn attached to the posterior capsule. Upon stretching of the capsule by the eye's ciliary muscles, the haptics and hence this periphery is twisted apart to increase the volume of rear space and changes the pressure difference between the spaces. As a result, the curvature of the membrane and accordingly, the refractive power of the lens, changes.

Another approach to varying the focus of an IOL is to form a conventional hard intraocular lens with a flexible outer surface made from a material such as silicone. Water is then injected in between the conventional hard portion of the lens and the flexible outer surface of the lens. The water will stretch the outer flexible layer to change the radius of curvature of the intraocular lens and thereby change the accommodation of the lens. One disadvantage of this approach is that a fluid source, a fluid pump and a flow control valve all must be provided within close proximity to the lens. As the area around the crystalline lens of the eye is quite confined, most of the fluid injection components have to be provided on the lens itself. Further, an energy source must be provided to pump the fluid. As there is no mechanical force generated in the eye that is strong enough to pump the fluid, an external power supply is required to run the pump. Such an external power supply is usually implemented using a battery which has a limited life cycle.

A further approach that has been used to vary the accommodation of an IOL is the coating of a conventional IOL with a liquid crystal material. A voltage source is applied to the crystal material to polarize the crystals. Once the crystals are polarized the refractive index of the crystalline material changes thereby changing the accommodation of the IOL. One principal disadvantage of this type of system is the relatively large amount of energy that is required to polarize the liquid crystal material, on the order of 25 volts. As there is no known manner of generating that level of voltage within the body, an external power source, such as a battery, is therefore necessary.

Some conventional accommodating IOLs rely on a solid curved surface to provide refraction. As such the force required for a change of curvature significant enough to induce an increase in diopter and accommodating power is much larger than that provided by the ciliary muscles especially in an aging lens. Other accommodating IOLs involve a displacement of the whole IOL along the optical axis to create accommodation. This does not only require a relatively larger force but also fails to deliver larger changes in diopter due to the lack of space in the anterior chamber.

The above described and other prior attempts to provide an intraocular lens with variable accommodation are generally complex systems. These complex systems are costly and difficult to manufacture and often times impractical to implement in the eye of a human. Therefore, current accommodating lenses provide little accommodating power (about 1 to 2.5 diopters "D"). For purposes of this art, it is to be understood that a multi-focal lens is not necessarily an accommodating lens, cf., U.S. Pat. No. 7,229,475. A true accommodating lens which more nearly mimics natural lens accommodation should have at least about 4 D, preferably at least about 6 D or more of accommodating power. In addition, multifocal IOLs provide a limited number of distances at which vision is adequate. In contrast, accommodating IOLs allow the patient to achieve good vision at any distance by providing a continuum of lens focal lengths to meet the wearer's needs. Therefore, a need exists for a simple IOL with greater levels of accommodating power that relies only on the forces provided by the human eye for operation.

SUMMARY OF THE INVENTION

The present invention addresses the shortcomings of prior art lenses and lens assemblies through the use of a novel refraction system based on the interface naturally created between first and second immiscible fluids or liquids (sometimes designated "I" and "II"). A significant change in refractive power can be achieved in a practice of this invention with application of minute forces and force changes e.g., by the ciliary muscle or ciliary body, without the need for movement of the IOL through the optical axis.

An accommodating IOL of the present invention generally comprises a lenticular chamber where two immiscible liquids are in contact with each other forming a meniscus. The interface between the two liquids provides the refractive surface that bends light into a focal point on the retina. The meniscus curvature and thus the focus of the lens is changed by applying pressure on the periphery of the lens generally by means of the lens haptics. A very small force, by ciliary muscle contraction applied to the haptics, is required to cause a significant change in meniscus curvature, which in turn changes the diopter of the lens to provide focus on objects at various distances. The force is transmitted from the ciliary muscles to the meniscus through the haptics. The haptics may be formed into several configuration including C-loop, modified C-loop, square, disk-like, plate, etc.

In a preferred practice of this invention the haptics themselves are at least partially hollow having fluid-containing haptic internal chambers, the haptic chambers being in fluidic communication with the lenticular chamber or lens body such that displacement of the haptic, e.g., posteriorly, causes some of fluid I or II to flow into the lens body and enhance, increase or amplify the accommodation obtained. In this aspect of the invention either or both of the visually transparent posterior and anterior walls which define the lenticular chamber are flexible or stretchable such that they can be displaced by one or the other of the fluids. In a preferred practice, only the posterior lenticular chamber wall is flexible or stretchable permitting it to be posteriorly displaced when fluid from the haptic chamber flows into the haptic chamber. In this embodiment of the invention the hollow lens haptics are preferably rectangular in configuration preferably are two in number, and are disposed on opposite sides of the optic body.

A variety of liquids may be used for this invention. The most important parameters are clarity, surface energy, density, viscosity and refractive index. Virtually any liquid combination may be used. The accommodating power for a variety of liquid combinations was calculated based on the change in meniscus curvature. The following Table 1 summarizes some of those results. In a preferred practice of this invention, the densities of the respective liquids are substantially the same.

In another embodiment of this invention, the liquids are only optionally immiscible (i.e., they may be miscible). In that embodiment, the liquids would be separated by an optically acceptable membrane or film. The film would keep miscible fluids or liquids separated and would confine fluids I and II so as to produce a variable diopter change according to the invention. The film or membrane is applied to the edge of the discs so that mixing of the miscible liquids having differing refractive indices (RI) is prevented. In a preferred practice, the liquids (or more generally "fluids" since one of the liquids can be air) have substantially the same densities. By "substantially the same densities" herein it is meant densities of such similarity such that the fluids or liquids can be contained within an elongate, vertically-disposed, optical chamber and, being immiscible as described herein, the fluid (s) or liquid(s) have little or no tendency to "settle out" at the bottom of the chamber (or collect at the bottom of the chamber) due to gravitational forces and thereby maintain a separated, vertically-disposed relationship with respect to each other when the wearer is looking horizontally or at a distance.

TABLE 1

| Design | Liquid I | Liquid II | Change in Diopter (D per deg of deformation angle) |
|---|---|---|---|
| 1 | Normal saline (0.9%) RI = 1.331 | Silicone fluid RI = 1.433 | 7.5 |
| 2 | Normal saline (0.9%) RI = 1.331 | Silicone fluid RI = 1.454 | 9 |
| 3 | Normal saline (0.9%) RI = 1.331 | Silicone fluid RI = 1.501 | 11 |
| 4 | Normal saline (0.9%) RI = 1.331 | Silicone fluid RI = 1.520 | 15 |
| 5 | Normal saline (0.9%) RI = 1.331 | Acrylic fluid RI = 1.512 | 10.5 |
| 6 | Normal saline (0.9%) RI = 1.331 | Acrylic fluid RI = 1.536 | 12.7 |
| 7 | Normal saline (0.9%) RI = 1.331 | Organic oil RI = 1.467 | 7.5 |
| 8 | Normal saline (0.9%) RI = 1.331 | Organic oil RI = 1.502 | 10.5 |

The advantages of the method and accommodating IOL of the present invention not here-to-for known to the art are:
1. Stable refraction since the interface between two immiscible liquids is naturally stable due to free energy considerations.
2. The interface can be moved with minute forces. This allows a change of curvature with minimal forces from ciliary muscles and hence significantly larger diopter changes.
3. The design is relatively simple and similar to that of conventional IOLs. Essentially, square edges may be incorporated into the design to prevent posterior capsule opacification (PCO).

A lens of this invention affords true accommodation and substantially increased lens diopter changes not here-to-for known to the art.

Thus, in one aspect, the present invention is a method of obtaining diopter changes, by means of an accommodating IOL, of at least 2 diopters, preferably at least 4 diopters; and most preferably at least 6 diopters (up to 10 diopters or more) in response to an implanted IOL patient's physiologic demand for such change. In a very real sense, the present accommodation method and accommodating IOL apparatus closely mimics the lens focus adjustment and response of a young, healthy, pre-cataractous eye.

The term "capsular unit", as it is used in the present description and claims, refers to the posterior capsule, the zonules, and the ciliary body, which are interconnected and act in unison, forming in accordance with the present invention, a kind of cable whose varying tension provides the axial force applied to and utilized by the lens assembly of the present invention to achieve accommodation.

A lens of the present invention is a substitute for a natural lens after its removal from the eye, not only by enabling the eye to see better (or at all) after implantation of the assembly, but also by enabling it to accommodate and thereby bring into focus objects located at a continuum of distances. In order to achieve accommodation, the assembly is designed to be fixed in the posterior chamber, in the capsular bag or sulcus, with the resilient body axially abutting the posterior capsule or the sulcus.

The lens assembly of the present invention utilizes the natural compression and relaxation of the capsular unit or sulcus to impart an axial force on the resilient body in order to cause it to act as a lens whose radius of curvature, and therefore the refractive power it provides, varies depending on the magnitude of the force. In this way, the lens assembly cooperates with the natural operation of the eye to accommodate and to enable the eye to see objects more clearly at different distances.

The haptics element of the assembly according to the present invention may adopt any of a variety of designs known in the art, e.g. it may be curved or it may be in the form of a plate. In addition, the haptics element may be completely transparent or opaque. The haptics element of the lens assembly in accordance with the present invention may be made of a variety of possible rigid materials suitable for invasive medical use and known in the art to be used in the formation of haptics. As is noted above, in a preferred embodiment, the haptics are at least partially hollow, containing one of the fluids, and being fluidically coupled via a channel to the lenticular chamber or lens body.

The advantages provided by the accommodating lens assembly of the present invention are many. The lens assembly does not need to conform to the size or shape of the capsule, and is therefore free to take on a larger variety of designs. Furthermore, the capsule is sometimes damaged during the surgery to remove the natural lens, but the lens assembly of the present invention does not require that the capsule be completely intact in the form of a bag but merely that it remain reliably connected as part of the capsular unit. Another advantage arising from the lens assembly being positioned outside of the posterior capsule is that it remains unaffected by the permanent and unpredictable constriction that the capsule inevitably undergoes due to scarring following the surgery for removal of the natural lens, usually referred to as capsule fibrosis, which occurs in all patients and at varying degrees. For conventional accommodating IOLs relying on lens optic forward movement to provide accommodation, capsule fibrosis immobilizes IOLs and limits forward movement of the optic causing inconsistent clinical outcome and limited accommodation range. The IOL of the present invention does not require the optic to move forward.

Further, in one embodiment, the lens of this invention is foldable. In this embodiment the lens comprises optically-acceptable, foldable materials. Thus all of the advantages of a foldable IOL known to one skilled in this art are provided.

In addition to the above, the lens assembly of the present invention offers advantages such as a simple and inexpensive construction. The lens assembly of the present invention also provides the ability to accommodate within a vast range of refractive power, including the full range provided by the natural eye and much more if needed in case of other eye diseases such as age-related macular degeneration (AMD). Also, the lens assembly provides means for varying its sensitivity in response to the force applied by the capsular unit. In addition, the lens assembly is similar in design to conventional monofocal IOLs and can be implanted using existing surgical instruments and techniques. No special surgical skills or training is required.

BRIEF DESCRIPTION OF THE DRAWINGS

In order to understand the invention and to see how it may be carried out in practice, preferred embodiments will now be described by way of non-limiting examples with reference to the accompanying drawings in which:

FIGS. 22, 23 and 24 show a further embodiment of the present invention in side view, top view and section taken along line 24-24 of FIG. 23.

DETAILED DESCRIPTION OF THE INVENTION

Figure 1:
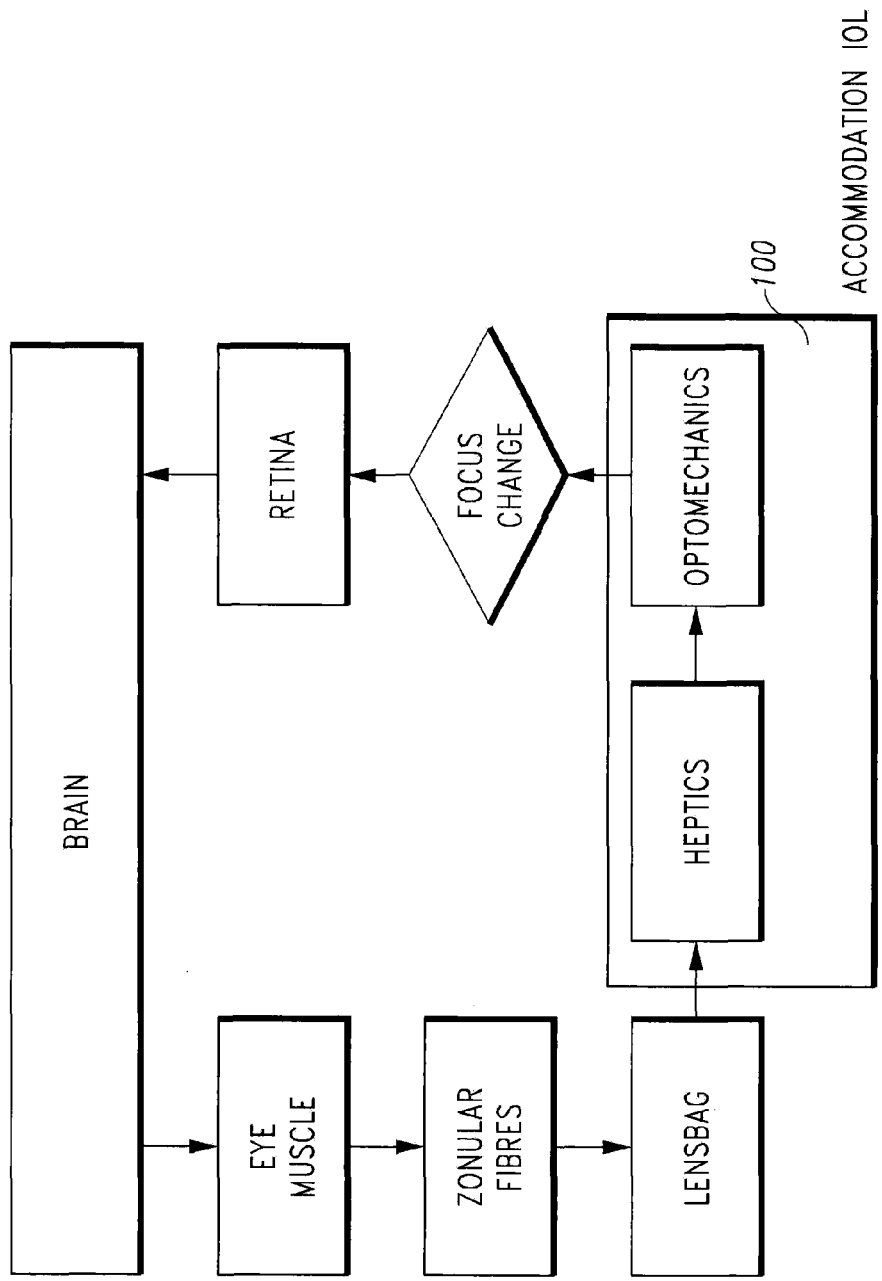
FIG. 1 is a flow chart showing the interaction between an accommodation IOL and a patient's optical sensory mechanism to provide improved visual acuity.
Figure 2:
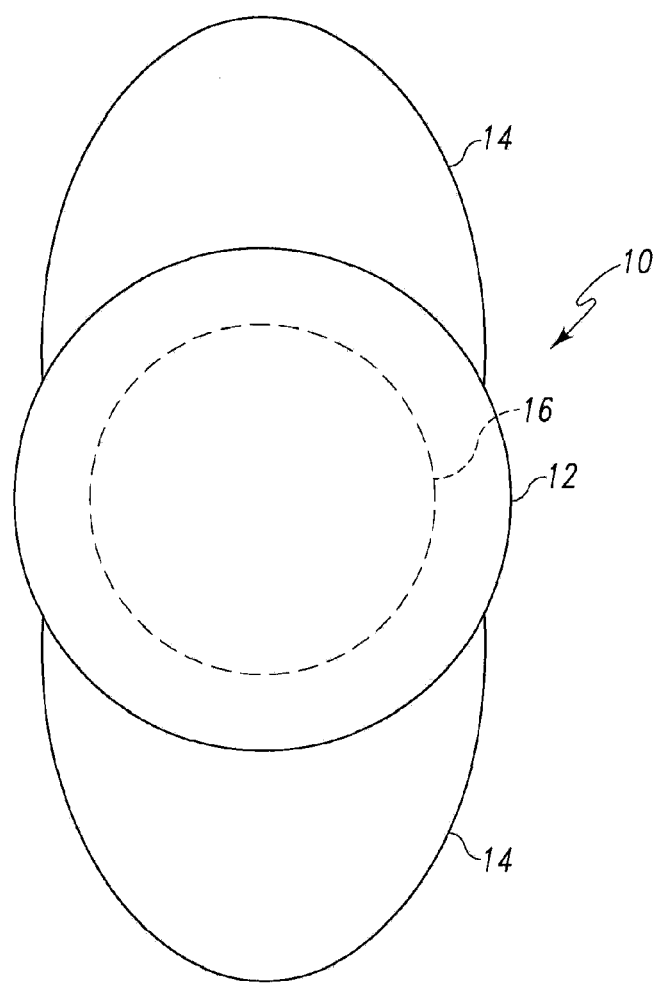
FIG. 2 is a front view of an Interfacial Refraction Accommodating Lens or Lens Assembly (IRAL) in accordance with the present invention.

The basic principles of accommodating lenses are, of course, well known to one skilled in the art. These principles are illustrated at FIGS. 1 and 2 (and associated disclosure at column 4 line 20 through line 52) of U.S. Pat. No. 5,489,302 that disclosure being specifically incorporated by reference herein.

Generally, in one aspect, this invention is an implantable interfacial refraction ophthalmic lens (IRAL) assembly or apparatus which adjusts its focal distance in response to changing physiologic needs of the user of said lens (e.g., a patent in which the lens has been implanted.). The lens comprises a flexible optic chamber, lens body, or optic and cooperating haptics. The optic chamber is defined by opposed, substantially parallel, visually transparent, generally circular, elastic or stretchable discs or walls, which are flexibly coupled at their edges and spaced apart to define a closed fluidic chamber. The fluidic chamber includes first and second liquids, the liquids having different refractive indices (the difference being ΔRI) and, in one embodiment, being immiscible and preferably of substantially the same densities so as to define a changeable or changing spherical or lenticular interface therebetween. The haptics are coupled to the edge of the optic chamber and to the fluidic chamber so that application of force to the haptics deforms the fluidic chamber, displaces fluid into the optic chamber and thereby changes the sphericity of the liquid interface. Thus, the focal length of the lens assembly changes in response to application of force to the haptics to change the visual focus of the user. Upon relaxation of the ciliary muscle force applied to the haptics, the haptics, having a natural bias to resist the applied force, return to their pre-application of force configuration or arrangement, the lens diopter thereby declining by, change in the shape of the I, II, fluid interface.

In one embodiment, the fluids are optionally immiscible and are separated by a visually transparent, flexible membrane which is sealed to the edge of the disc(s) to define flexible fluidic chamber and which prevents the fluids from mixing.

This invention also includes a method of correcting visual activity by the use of an accommodating IRAL, the method comprising the steps of:

replacing a defective natural lens of an eye of a patient in need of such replacement with an accommodating IRAL;

permitting the IRAL to accommodate the patient's need to change the focal point of the eye e.g., the retinal focus, by changing the diopter strength and thus the focal point of the IRAL wherein the diopter strength change of the IRAL is at least 2 diopters;

and wherein the IRAL employs liquids having different refractive indices to define to change diopter strength and thus the interface.

FIG. 1 is a flow chart showing the optomechanical principle which permit an accommodating lens e.g., an accommodation IOL, to interact with physiologic, optical signals to provide better near and distance visual acuity to a user of the lens. In short the brain instructs the muscular ciliary body (eye muscle) to contract. That muscular contraction applies a subtle, generally posteriorly-directed, force to the lens haptics (discussed below) via the zonular fibres. That force applied to the haptics causes the optical power of the accommodating lens to change thereby focusing in-coming light onto the retina with greater accuracy and with increased clarity. Box 100 shows generally the functions of the haptics and coupled optomechanics of an accommodating or accommodation IOL, such as a lens of this invention, in that process. The haptics center the IOL in the focal zone or focal axis of the eye and receive and transmit ciliary muscle force to the optic chamber or lens body (described in greater detail below). The haptics can be in direct contact with eye muscle if the accommodation IOL is implanted into the sulcus. The optomechanics of an accommodating IOL of the invention then converts the ciliary muscle force into diopter changes of the lens.

FIG. 2 is a front view of an interfacial refraction accommodating lens (IRAL) of the present invention. In FIG. 2 there is shown a lens assembly 10 comprising an optic chamber or lens body 12 and haptics 14. It will be understood that haptics 14 shown in FIG. 2 are only one possible haptic configuration, there being many others which will readily occur to one skilled in this art in view of this disclosure. Also shown within optic chamber 12 by a dotted circle 16, 16' is the position of the refractive surface (i.e. the interface between the two fluids) upon responding to the force exerted by the ciliary muscles.

Figure 3:
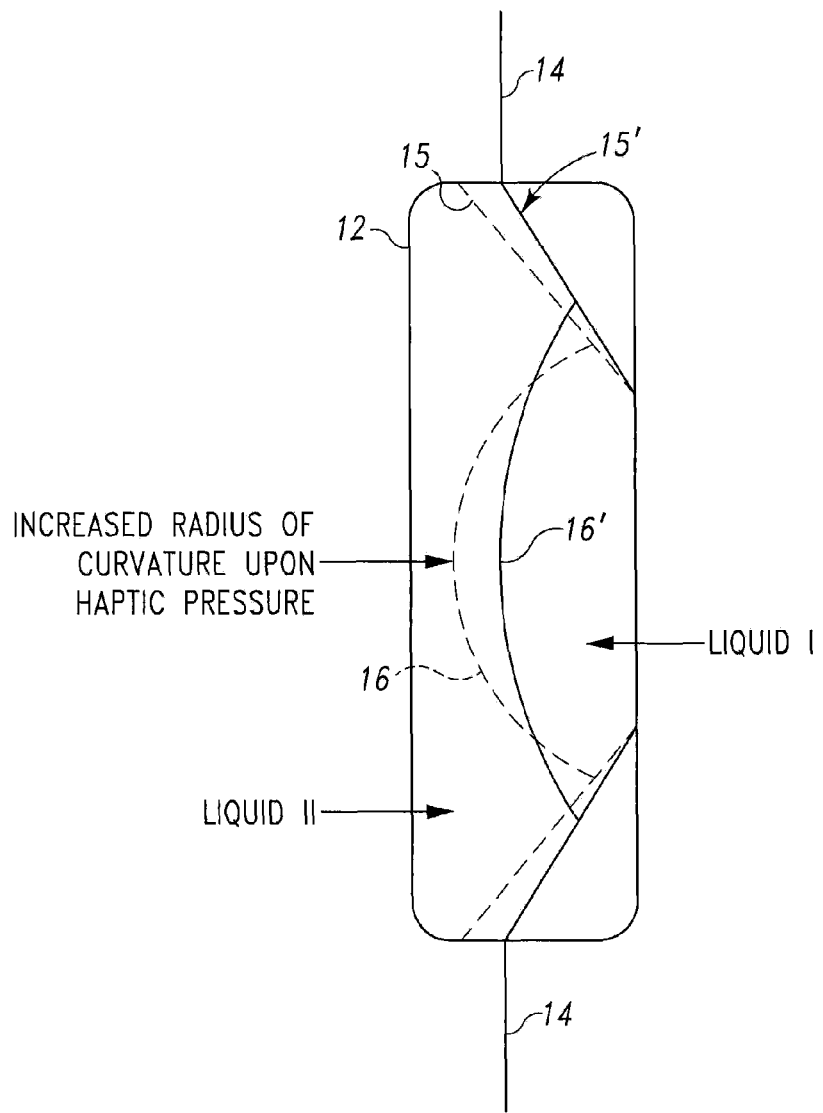
FIG. 3 is a cross-sectional view of the IRAL shown in FIG. 2.

FIG. 3 is a cross-sectional view of the IRAL shown in FIG. 2 showing the relationship between haptic deformation or displacement angle 15, 15' and the change in interfacial radius of curvature 16, 16' achieved by very small haptic deformation angle changes. The change in the shape of the interface 16 shown in FIG. 2 illustrates the increase in radius of curvature of the refractive surface upon changes in haptic pressure. Changes in haptic pressure are obtained by changes in the deformation of the haptics which, in turn, result from increased pressure of the ciliary muscle or capsular bag. As is shown, the radius of curvature of the interior envelope 16, 16' changes in response to haptic deformation angle changes. That change in radius of curvature in conjunction with the Liquids I and II (having a refractive index characteristics detailed below) create substantial dioptric changes for very small ciliary muscle movement(s). Changes in diopter per degree change in deformation angle for various Liquids I and II are shown in Table 1 above. Clearly the invention provides diopter changes which are substantially in excess of anything disclosed in the prior art. Thus, for example, diopter changes (and accommodation as discussed above) in the range of four diopters, preferably six diopters, and most preferably about 7.5 diopters or more are obtained in once practice of this invention.

Figure 4:
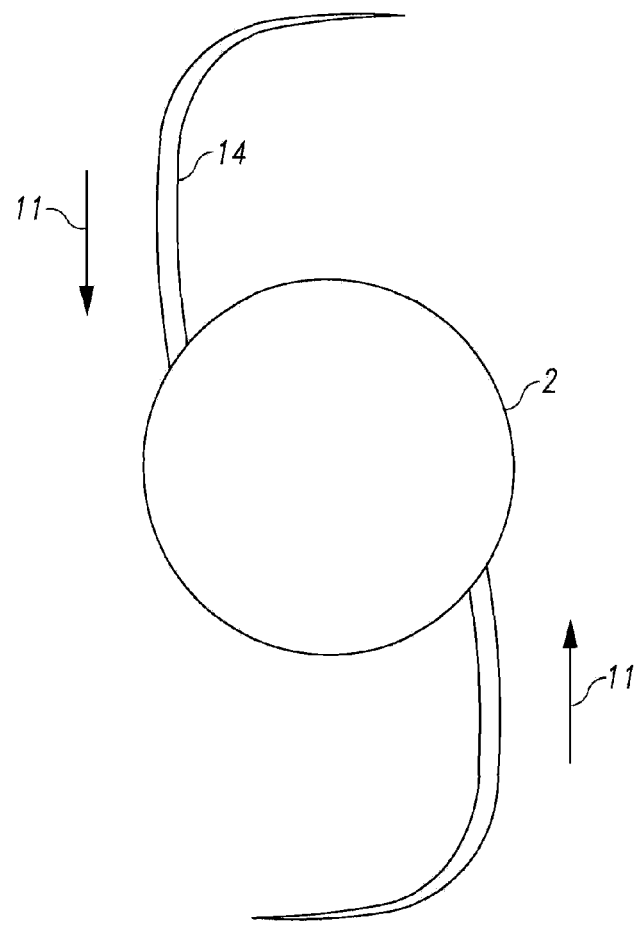
FIG. 4 is a perspective view of a second embodiment of the present invention in which the direction of the application of force to the haptics by the ciliary muscle is illustrated by arrows (11). The accommodating lens of FIG. 4 also has a different haptic configuration from the lens of FIGS. 1 and 2.

FIG. 4 is a perspective view of another embodiment of the present invention in which the direction of application of force, e.g., by a ciliary muscle, is shown at arrows 11. Haptics 14 are of a further partial loop variation consistent with the teachings of this invention. Further embodiments of optic chamber, fluid chamber, or lens body 12 are discussed below.

Figure 5:
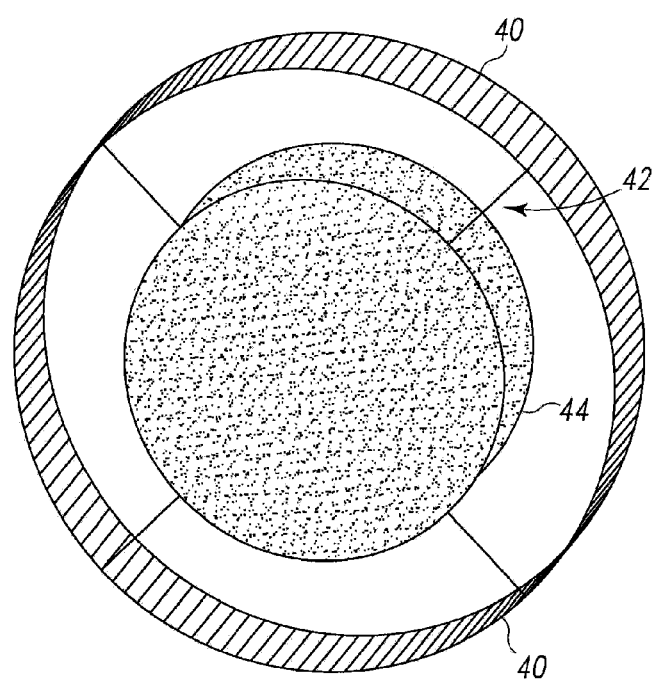
FIG. 5 is a perspective view of a piezoelectric or electrical accommodating lens embodiment of the present invention.
Figure 6A:
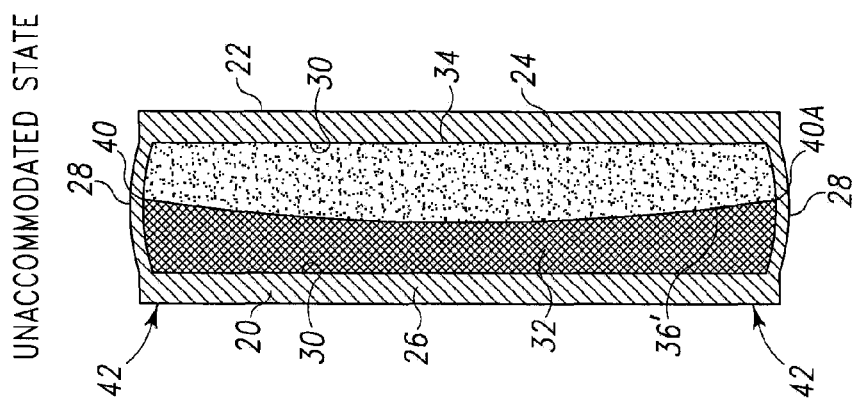
FIG. 6A shows an IOL of this invention in the accommodated state and 6B shows the same IOL as is shown in FIG. 6A in an unaccommodated state.
Figure 6B:
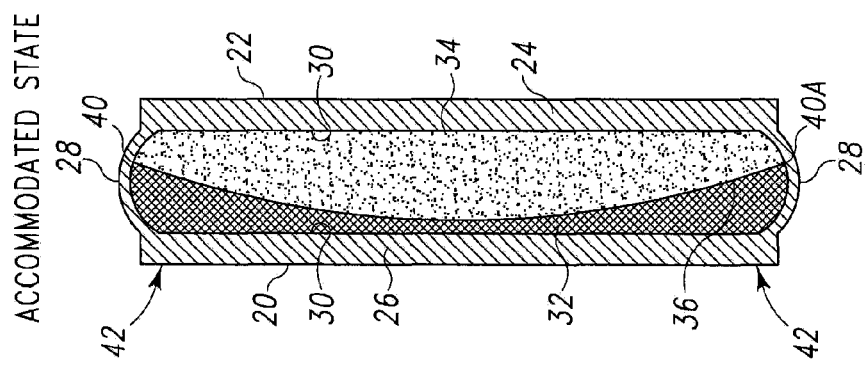

FIG. 5 illustrates an electrical or piezoelectric design or approach to the present invention. As is noted, a transducer element or circular haptic 40 is coupled or connected via the connecting or coupling element 42 to fluid chamber 44. In accordance with this approach, movement of the transducer element-haptic 40 by the user's ciliary muscle causes an electrical signal to be transmitted, via conducting element 42 to fluid chamber 44. Accommodation in the eye is induced by the contraction of ciliary muscles (not shown) and capsular bag (not shown). A method of this invention involves a transducing element 40 sensing the ciliary muscle force and generating an electrical current or voltage through lens chamber 44. The electrical voltage induces a change in surface energy along the surface of chamber 44 which in turn causes a steepening of the curvature of the interface between the two liquids. In one aspect, then, this invention is an accommodating IOL where the change in the interface curvature is directly induced by the electrical impulse generated by the ciliary muscle during contraction. In this embodiment, the haptic is made from a conducting material. A conducting element could also be embedded in the haptic.

A transducer capable of converting the ciliary muscle or capsular bag movement into an electrical signal is used to effectively change the shape of the meniscus and allow accommodation. The transducer can be a piezoelectric device, a force sensor, an actuator or any other element capable of converting a force into an electrical signal. The haptics may be made from a force sensing element. The haptics may be formed into several configuration including C-loop, modified C-loop, square, disk-like, plate, etc.

The materials chosen to practice this invention will be readily apparent to one skilled in this art. In one embodiment, haptic materials may include PMMA, PVDF, PP, or other polymers. Optic chamber 12 materials can include hydrophobic acrylic polymers or copolymers (HAC), hydrophilic acrylic polymers or copolymers, silicone polymers or copolymers (PDMS) or other polymers. Preferred polymers include PDMS or HAC. (12 and 16 are made from the same material). As is noted the relationship between refractive indices of Liquids I and II are required in order to obtain the advantages of the present invention.

Reference is now made to FIG. 6-14 in which several further embodiments of this invention are shown. In these FIG. 6, the anterior side of the implant, lens body or lens assembly 20 is generally to the left; posterior 22 generally to the right. The lens body or optic chamber generally comprises discs 24, 26 which are flexibly coupled at their edges 28. As is shown flexible coupler or sidewall 28 is compressible and provides an annular connection between discs 24, 26, coupler 28.

Because discs 24, 26 are spaced apart along the focal axis of the eye (when implanted) a closed fluidic chamber 30 is defined. Chamber 30 contains immiscible liquids 32, 34 having differing refractive indexes according to this inventor. Generally, the higher refractive index liquid will be posteriorly disposed in lens body 34, with the lower refractive index liquid 32 being anterior, although the opposite arrangement may be used in some embodiments.

Due to the immiscible liquids 32, 34 a spherical curved interface 36 is formed. At its perimeter the interface has a fixed contact angle 40A at the interface to the implant sidewall 28. The curvature of this liquid interface depends on the properties (surface tensions) of the liquids and the implant material. It corresponds to an energy minimum. Force from the eye muscle is transmitted to the implant by haptics schematically shown by arrows 42, the bolder arrow indicating greater force. This applied force deforms a sidewall 28. Because of the fixed contact angle 40 a change in sidewall inclination will change the radius of the liquid interface 36 (an energy minimum is attained). A change in radius will lead to a change in optical power i.e., diopter rating of the device 10.

In this manner the focal length of the IOL will change to provide a better focus of impinging light on the retina (not shown).

Figure 7A:
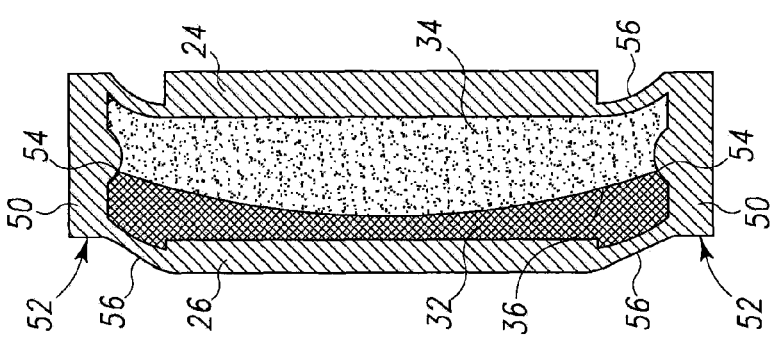
FIGS. 7A and 7B, show accommodated and unaccommodated states of yet a further version of an IOL of this invention.
Figure 7B:
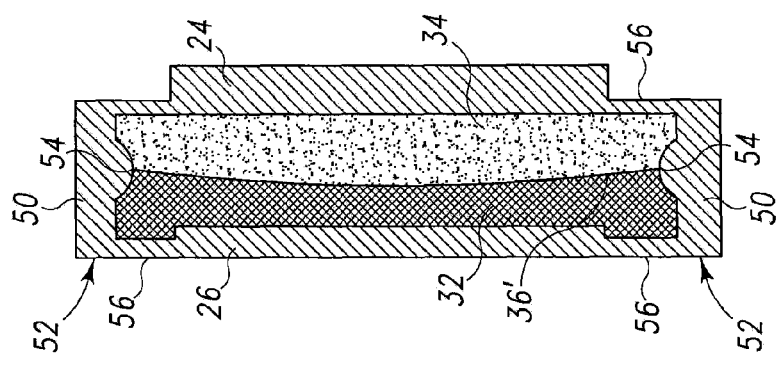

In FIG. 7, a variation is shown in which the force from the eye muscle is transmitted to the implant by haptics to a displaceable annular sidewall 50. The applied force shown by arrows 52 pushes the liquid interface along the variable curved sidewall 50. This is done by deforming hinge-like structure 56, which is integrated into the implant. One can think of other possible mechanical solutions to achieve the movement of the liquid interface along the structured sidewall 50. As the inclination of the sidewall 54 changes, the liquid interface will adapt its curvature to achieve the fix contact angle. This corresponds to an energy minimum. A change in radius will lead to a change in optical power of the device.

Figure 8:
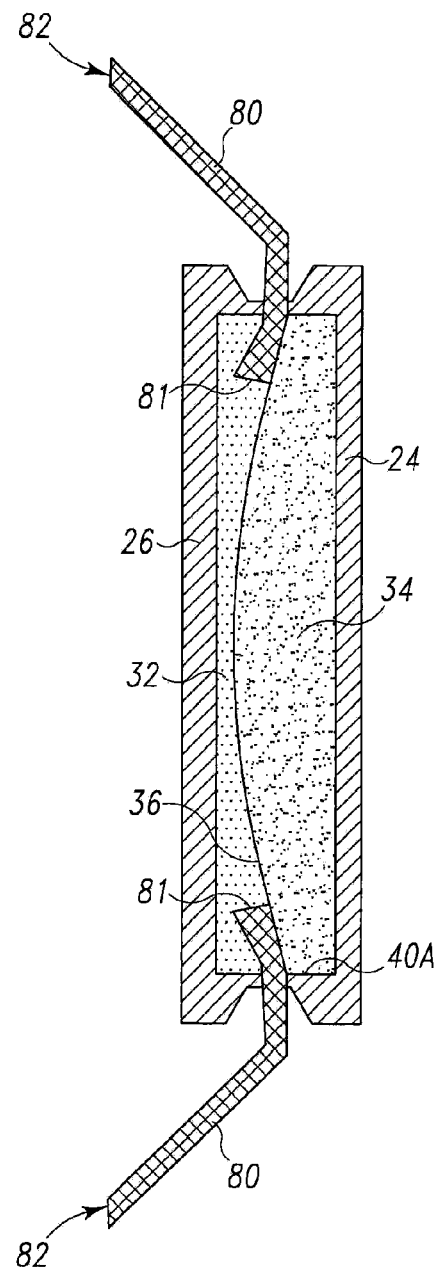
FIG. 8 shows yet a third accommodating IOL of this invention in cross section.
Figures 9, 10:
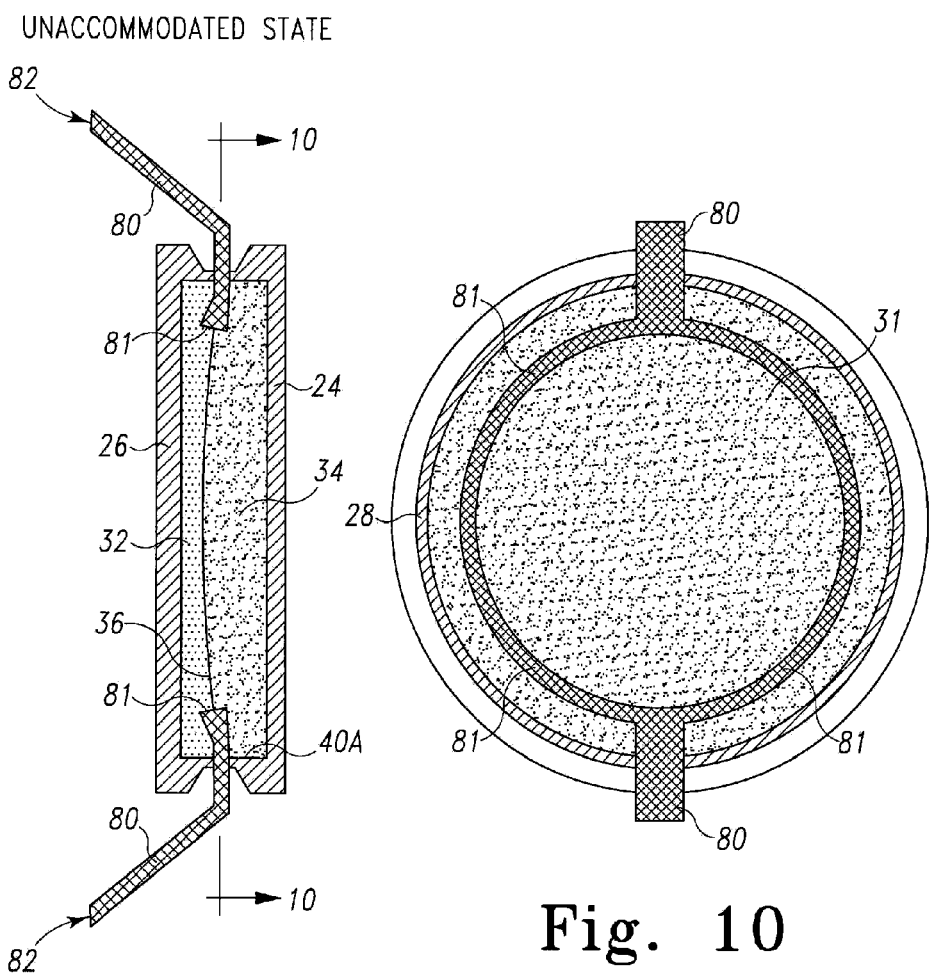
FIG. 9 is an IOL as shown in FIG. 8 in an unaccommodated state i.e. the haptics not being posteriorly-disposed.
FIG. 10 shows the lens of FIG. 9 in section taken along line 10A-10A of FIG. 9, the direction of view being to the right (posteriorly).
Figure 11:
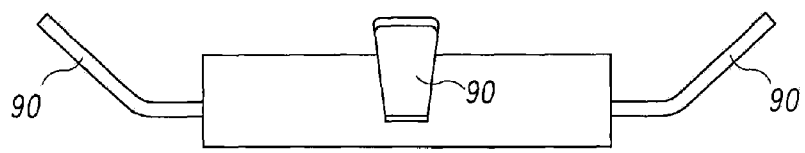
FIGS. 11-13 illustrate in side view, a top view, and in section along line 13-13 of FIG. 12, respectively, a further accommodating IOL of the present invention.
Figure 12:
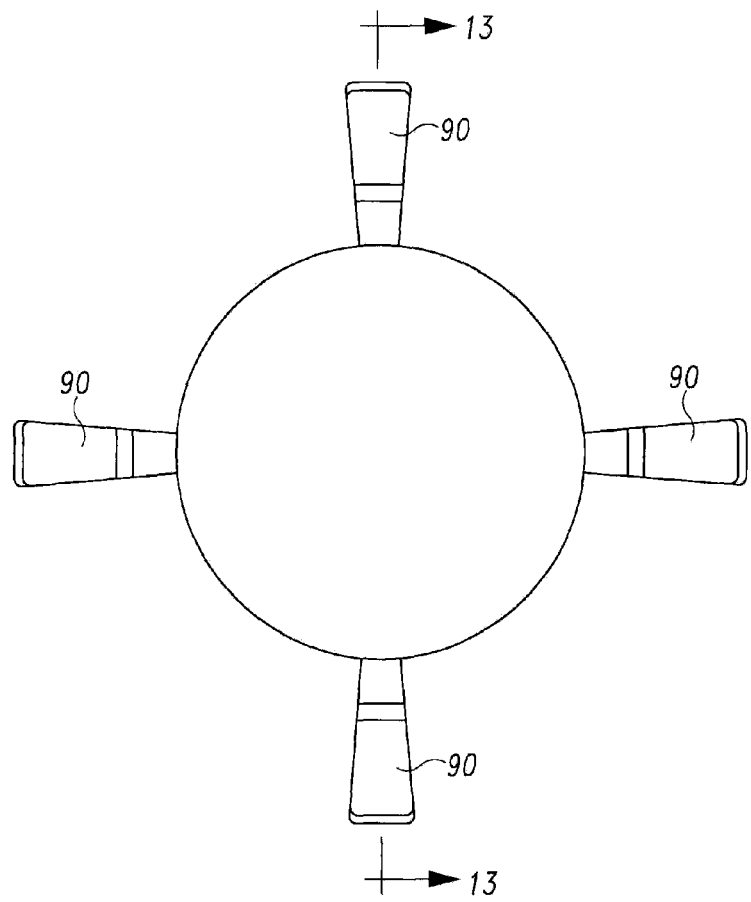
Figure 13:
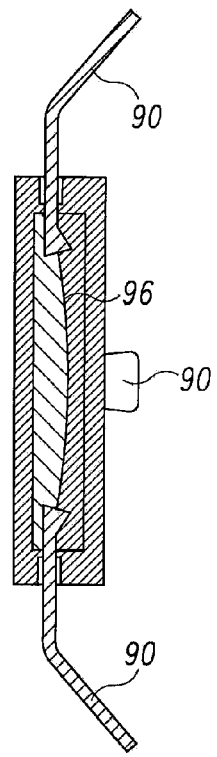

Due to the immiscible liquids a spherical curved interface 36 is formed. At its perimeter 54 the interface has a fixed contact angle to a movable ring structure within the implant 10. The curvature of this liquid interface depends on the properties (surface tension) of the liquids and the implant material. The force from the eye muscle is transmitted to the implant by haptics. FIGS. 8, 9, and 10 illustrate a further embodiment of the invention. Haptics 80 in this embodiment are interiorly coupled to a moveable interior ring 81. Force applied at arrows 82 moves the ring structure 81 within the implant. The movable ring structure could be made out of a different materials (e.g., having a high stiffness) than the implant. As the ring structure is swept across the liquid interface a certain radius of the liquid interface will be formed that corresponds to an energy minimum. The change in radius thus will lead to a change in optical power of the implant.

Figure 14:
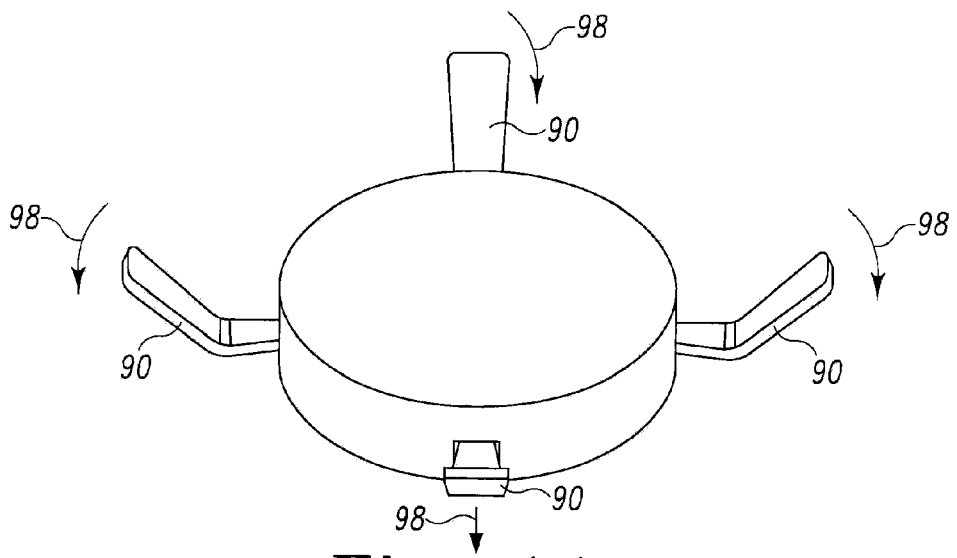
FIG. 14 shows the IOL of FIG. 13 in an accommodating state, the haptics being slightly bent, depressed or moved in the direction of the arrows toward the bottom of the figure.

FIG. 11-14 illustrates a lens where both the static power and accommodative power also are generated by the interface between the two liquids. The implant is designed such that the haptics are in contact with the sulcus. Designs where the implant sits in the lens bag are also feasible. In the design four haptics 90 are shown, which are in contact with sulcus. One can think of designs with less or more haptics. In the accommodated state the contracted ciliary muscle pushes the haptics in direction of the vitreous. This will lead to a movement of the ring within the implant in the opposite direction. The liquid interface will form a certain radius which corresponds to an energy minimum (depending on the design of the ring structure and materials involved). Arrows 98 generally show the direction of shift in haptic 90 deformation to achieve the accommodated or accommodation state. In FIG. 14 the curvature of the liquid interface is increased compared to the unaccommodated state 96 (FIGS. 11, 12, and 13) and the optical power of the implant increases.

Computation of Lens Parameters

Results were obtained using the following formula (paraxial approximation)

$$\text{Radius Liquid Interface} = \frac{\Delta RI}{\text{Static Power}}$$

Results were obtained using the following formulas (paraxial approximation)

Radius of Liquid interface in unaccommodated state:

$$R_1 = \frac{\Delta RI}{\text{Static Power}}$$

Radius of Liquid interface in accommodated state:

$$R_2 = \frac{\Delta RI}{\text{Static Power} + \text{Accommodation}}$$

Sidewall deformation angle $$\text{Deformation Angle} = \arcsin\left(\frac{D_{Lens}}{2R_1}\right) - \arcsin\left(\frac{D_{Lens}}{2R_2}\right)$$

Using Taylor approximation this formula can be further simplified to:

$$\text{Deformation Angle} \approx \frac{D_{Lens} \cdot \text{Accommodation}}{2 \cdot \Delta RI \cdot 1000} \frac{180°}{\pi}$$

where $D_{lens}$ is in mm and Accommodation in D.

TABLE 2

| Static Power [D] | ΔRI = 0.1 Radius Liquid Interface [mm] | ΔRI = 0.23 Radius Liquid Interface [mm] |
| --- | --- | --- |
| 10 | 10.0 | 23.0 |
| 12 | 8.3 | 19.2 |
| 14 | 7.1 | 16.4 |
| 16 | 6.3 | 14.4 |
| 18 | 5.6 | 12.8 |
| 20 | 5.0 | 11.5 |
| 22 | 4.5 | 10.5 |
| 24 | 4.2 | 9.6 |
| 26 | 3.8 | 8.8 |
| 28 | 3.6 | 8.2 |

TABLE 3

| Accommodation [D] | ΔRI = 0.1 Sidewall Deformation Angle [°] | ΔRI = 0.23 Sidewall Deformation angle [°] |
| --- | --- | --- |
| 6 | 14.4 | 4.7 |
| 10 | 27.3 | 7.9 |
| 20 | not possible | 16.3 |

TABLE 4

| Static Power [D] | ΔRI = 0.13 Radius Implant [mm] |
| --- | --- |
| 10 | 13.0 |
| 12 | 10.8 |
| 14 | 9.3 |
| 16 | 8.1 |
| 18 | 7.2 |
| 20 | 6.5 |
| 22 | 5.9 |
| 24 | 5.4 |
| 26 | 5.0 |
| 28 | 4.6 |

TABLE 5

| Accommodation [D] | ΔRI = 0.1 Sidewall Deformation Angle [°] | ΔRI = 0.23 Sidewall Deformation angle [°] |
| --- | --- | --- |
| 6 | 10.4 | 4.5 |
| 10 | 17.5 | 7.5 |
| 20 | 36.9 | 15.1 |

TABLE 6

| Static Power [D] | ΔRI = 0.13 Radius Implant biconvex [mm] |
| --- | --- |
| 10 | 26.0 |
| 12 | 21.7 |
| 14 | 18.6 |
| 16 | 16.3 |
| 18 | 14.4 |
| 20 | 13.0 |
| 22 | 11.8 |
| 24 | 10.8 |
| 26 | 10.0 |
| 28 | 9.3 |

TABLE 7

| Accommodation [D] | ΔRI = 0.1 Sidewall Deformation Angle [°] | ΔRI = 0.23 Sidewall Deformation angle [°] |
| --- | --- | --- |
| 6 | 10.4 | 4.5 |
| 10 | 17.5 | 7.5 |
| 20 | 36.9 | 15.1 |

Figure 15:
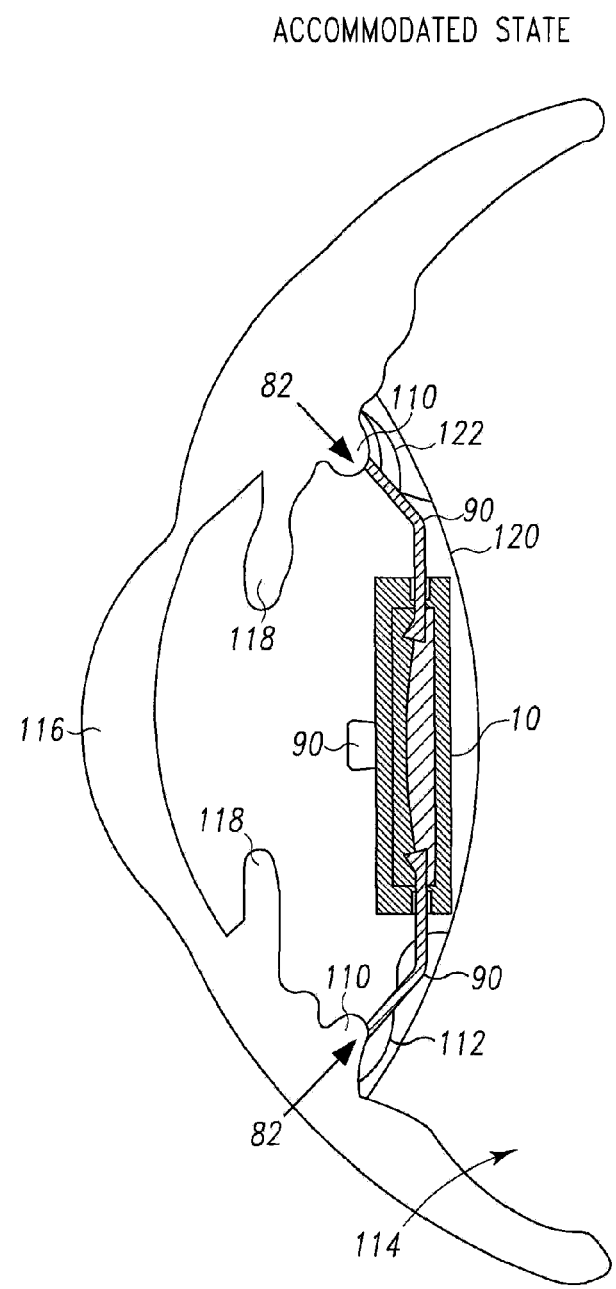
FIG. 15 shows an implantation site of an IOL of the present invention, the IOL being in an accommodated state.
Figure 16:
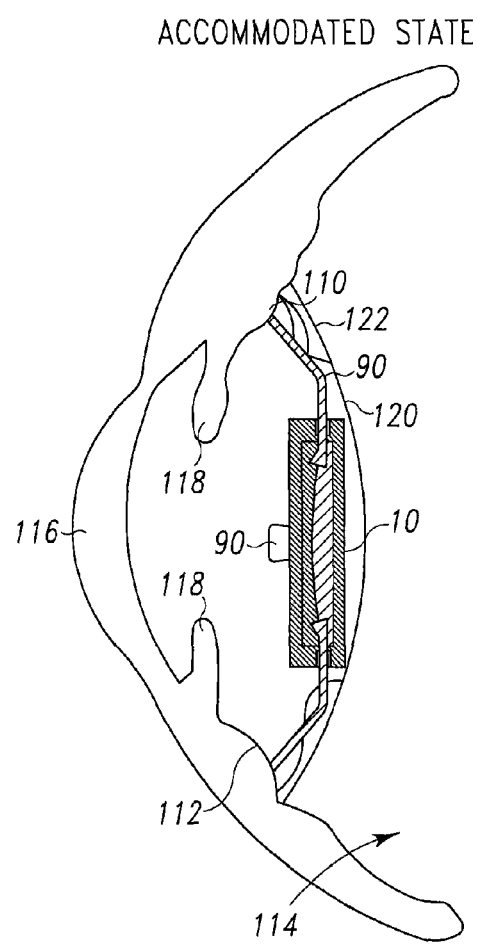
FIG. 16 shows the IOL of FIG. 15, as implanted, in an unaccommodated state.

FIGS. 15 and 16 show generally the implant site in the eye where a lens of this invention would be located. Anterior is to the left while posterior is to the right. Impinging light enters from the left and is to be focused upon the retina (not shown). FIG. 15 shows, e.g., a lens of FIGS. 9-14 with the contracted ciliary muscle 110 applying force to haptics 90—so as to deform the surfaces of the immiscible liquids in lens body 10 to change of optical characteristics of the lens, i.e., to accommodate the optical need of the implant patient. The sulcus 112, vitreous 114 cornea 116, iris 118, collapsed lens bag 120, and zonules 122 eye structures are shown. FIG. 16 shows the same implant location and IOL with the ciliary muscle relaxed (an unaccommodated state).

Figure 17:
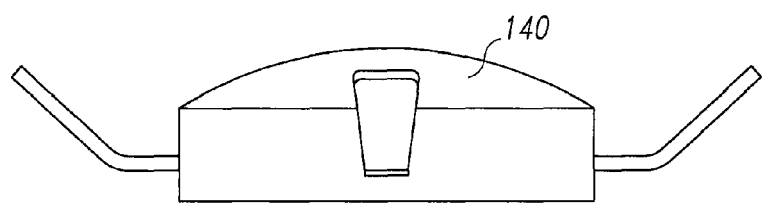
FIGS. 17, 18 and 19 show in side-view, in top view, and in section, respectively, the further embodiment of an IOL of this invention.
Figure 18:
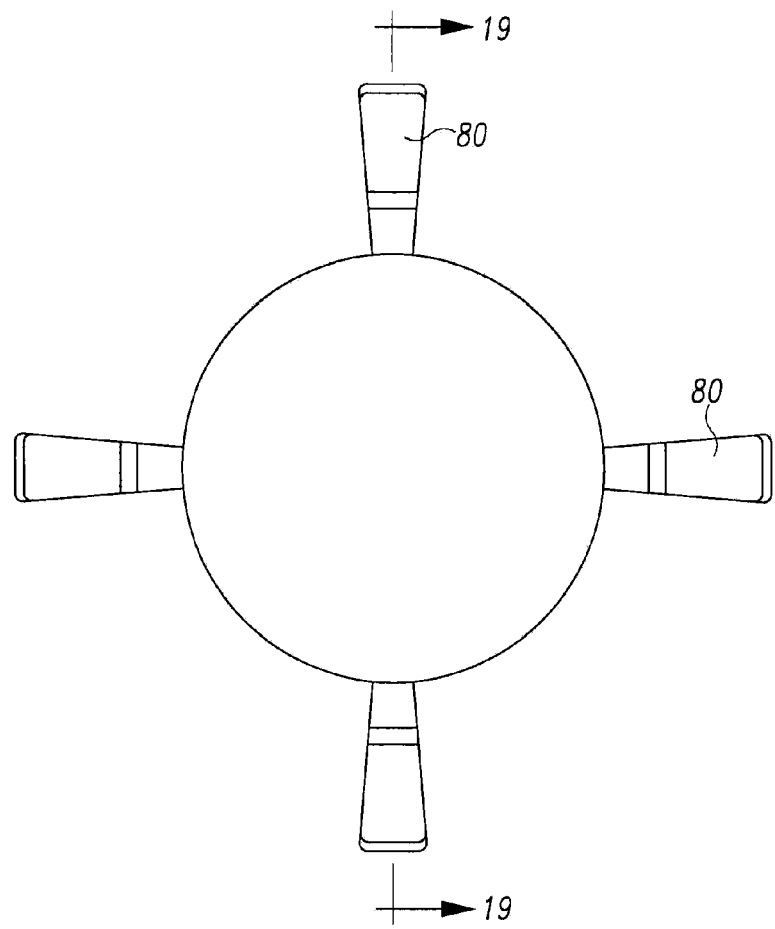
Figure 19:
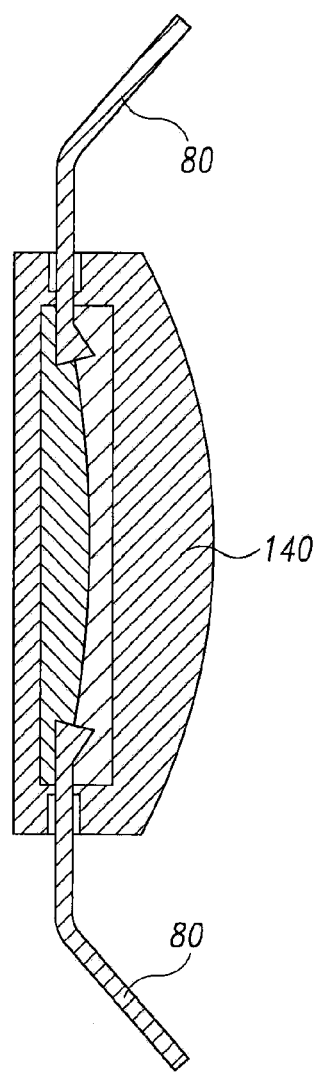

FIGS. 17-19 show a variation in which an anterior uniconvex lens 140 is used. All other structural elements are the same.

Figure 20:
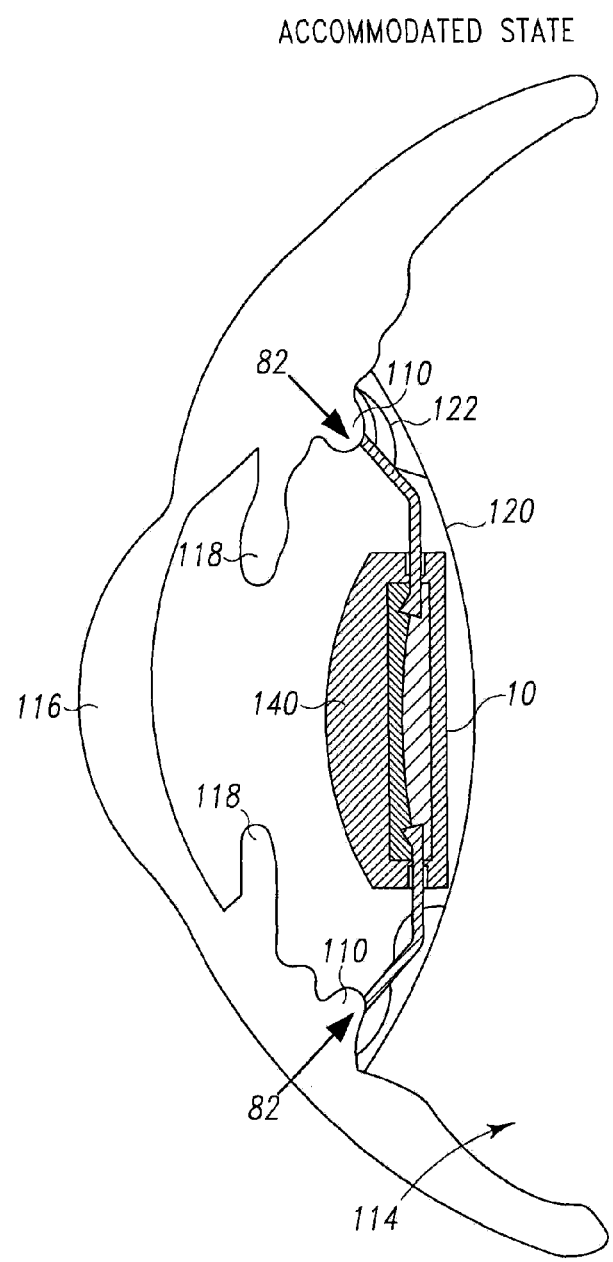
FIGS. 20 and 21 show an implantation site of the IOL of FIGS. 17-19 in an accommodated, and unaccommodated state, respectively.
Figure 21:
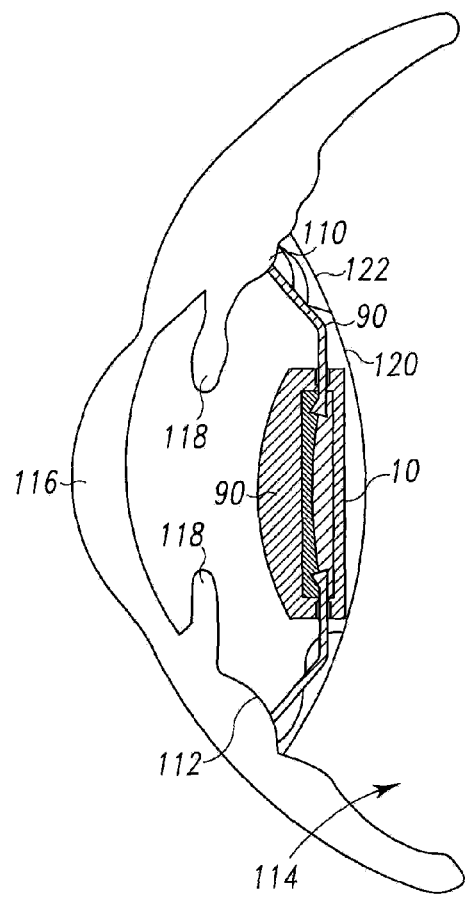

FIGS. 20-21 shows the lens of FIGS. 17-19 as implanted.

Figure 22:
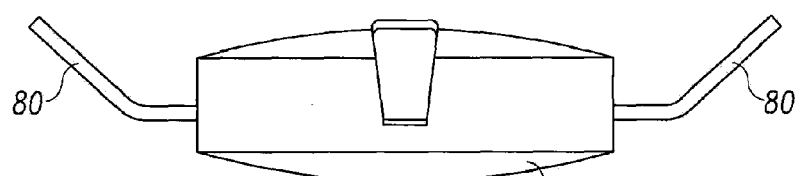

FIGS. 22-24 shows an equiconvex or biconvex IOL 160 design of this invention. An implantation view would be similar to that as shown in FIGS. 15 and 16.

FIGS. 25-26, and 27A-D show a preferred embodiment of this invention in which one or the other of fluids I, II are contained within hollow lens haptics and is displaced into the optic body by e.g., ciliary muscle contraction. The lenses shown are generally viewing toward the bottom of the page.

Figure 25:
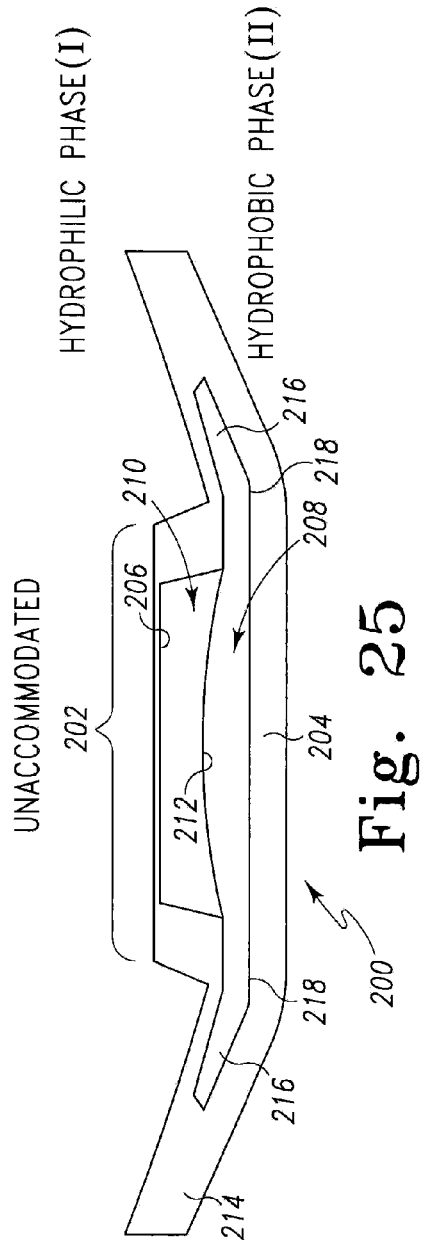
FIGS. 25-26 and 27A-D show a further embodiment of the present invention in which lens haptic fluid chambers are coupled to the lens body and which by moving posteriorly (or anteriorly) change the lens focus.

FIG. 25 shows in section an unaccommodated lens 200 comprising an optic chamber or lens body 202 defined by transparent anterior 204 and posterior 206 lens walls. Hydrophobic and hydrophilic liquids 208, 210 are contained within optic chamber 202 and define an interface 212 according to this invention. Haptics 214 are at least partically hollow, defining haptic chambers 216 which are fluidically coupled by a channel 218 to optic chamber 202.

Figure 26:
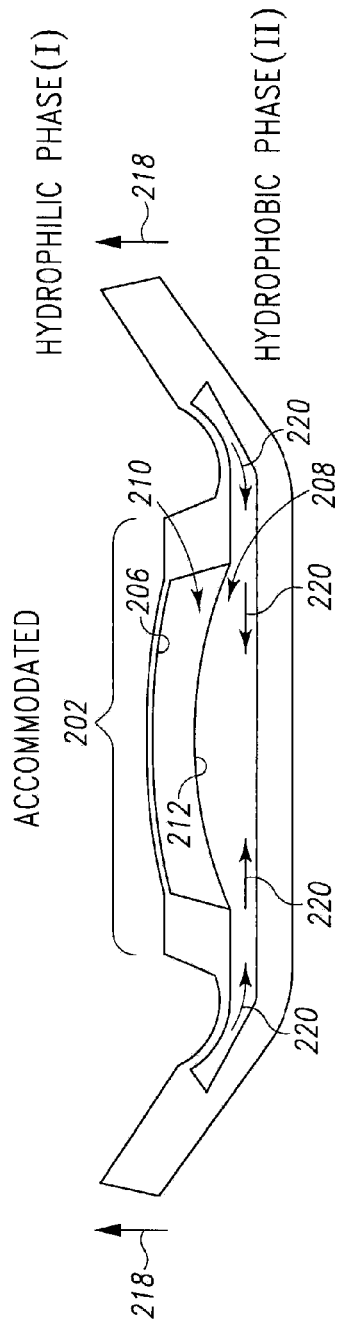
Figure 27:
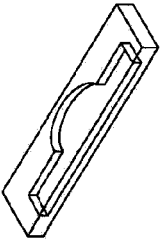

FIG. 26 shows the lens 200 of FIG. 25 in an accommodated state where posterior displacement of haptics 214 obtains the accommodation. As is shown, posterior lens wall 206 is flexible allowing it to bulge posteriorly permitting increased accommodation by increased change in the curvature defined by interface 212. Arrows 218 show the direction of haptic displacement while arrows 220 show the direction of fluid flow in response to haptic displacement. Although not shown, the reverse direction fluid flow occurs (i.e., into the haptic chamber 216) when the haptics in FIG. 26 are permitted to return to the configuration shown in FIG. 25. Thus, accommodation and relaxation of the accommodation are obtained.

FIGS. 27A-D illustrate in partial plan and partial section further embodiments of the lens shown in FIGS. 25 and 26. As is shown, rectangular, oppositely disposed hollow optics are used. Other lens body/haptic configuration will occur to one skilled in this art.

Accommodation Power Measurements

Figure 28:
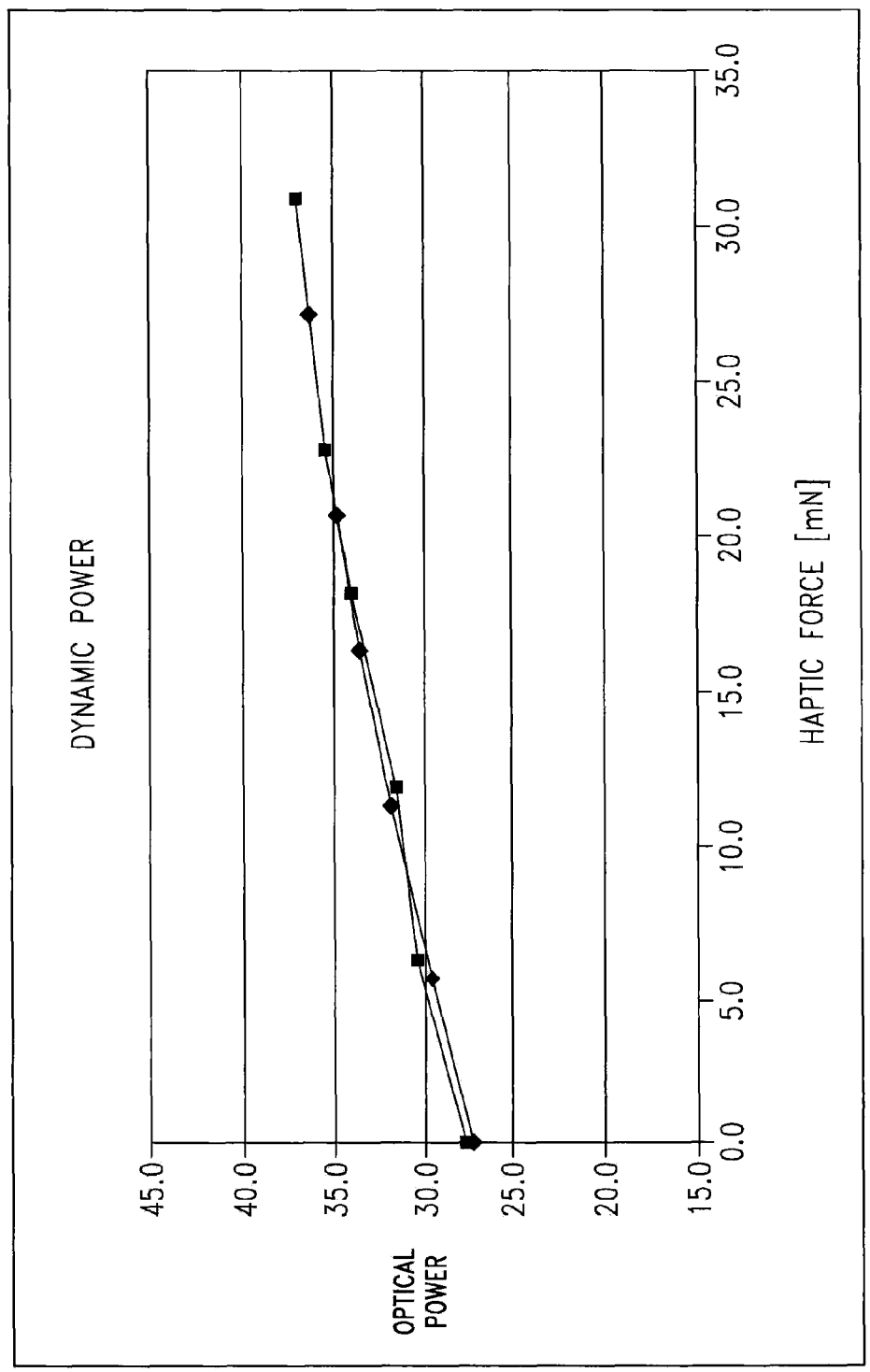
FIG. 28 shows a plot of Haptic forces vs. Optical power.

Selected designs were tested in a specially built testing device that simulates accommodation in the eye. The change in power of the IRAL lens was measured in response to forces exerted on the haptics simulating the natural accommodation process in the eye. Accommodation in excess of 10 D was observed (FIG. 28). In addition, the increase of refractive power was found to be instantaneous and almost proportional to the force exerted on the haptics. This represents a behavior similar to the natural crystalline lens of young humans.

Reference is made to Tables 2 through 7 above. The above mathematical construct in conjunction with the information contained in the tables permit one skilled in the art to design an accommodating lens of this invention which is uniquely applicable to a particular patient's vision needs. "Static Power" is a measurement of a lens's power required to provide correct visual acuity at a distance, such as for driving or observing sporting events. The accommodation provided by a lens of this invention is that the same lens also provides near vision correction, e.g., such as is required for reading. Thus for any given static power determined for a patient, the Tables show the radius of curvature that is obtained for any given differential in refractive index ($\Delta RI$) of liquids I and II (also 32, 34) contained within the optical chamber of lens body discussed above. Clearly, the greater the difference in refractive index ($\Delta RI$) the larger the radius liquid interface and the larger the permitted lens accommodation. Sidewall deformation angles are shown for various lens accommodations. The "$\Delta RI$'s" of 0.1 and 0.23 that have been used in the Tables are to be understood as exemplary, other such differences being useable and within the contemplation of the present invention.

It is noted above that in one embodiment of the present invention, fluids having differing refractive indices are used but which are miscible. In this structure the two liquids are separated by an optically-acceptable, flexible, or elastic membrane, film, or divider. The membrane would then define the interface or meniscus between the fluids (e.g., at 16, 16' in FIG. 3, 96 in FIG. 13, 36' 36 in FIGS. 6-9,) and thus the radius of curvature which determines the degree of accommodation. The membrane which separates fluids I and II would not be permeable by either fluid, would not be chemically affected by either fluid, and would be internally bonded to the edge of the optical chamber or lens body so as to prevent the liquids from mixing.

It is to be noted that an IRAL of the present invention is a completely hermetically sealed structure. The present IRAL are robust, intended for long term implantation, providing many years of near-natural lens accommodation for the patient.

IRALs of this invention are, in a preferred embodiment, foldable. In the foldable embodiment of this IRAL the lens obtains small incision implantation and other medical advantages which foldable IOLs provide. To be foldable, materials chosen for the various lens structures must have relative flexibility or rigidity so as to perform the their optical intended function(s) and to provide structural integrity while also permitting the entire structure to be sufficiently soft or flexible to be stored in a folded state and to unfold when inserted in folded or rolled fashion through a small incision during the implantation procedure.

With the above structural and medical functions and the mathematical construct in mind, the selection of materials for the various lens structures will be suggested to one skilled in this art. Optically-acceptable materials provide the requisite light transmissivity, depending upon their function, and can be implanted in the eye for long periods of time. Immune response, biodegradability (or absence thereof), and various other physiologic factors all must be considered in selecting such materials. The acrylate family of polymers, and polymer chemistry, are suggested for many of the structure of this invention.

The following patents and published patent applications are incorporated by reference herein:
US 2004/0181279
U.S. Pat. No. 7,025,783
U.S. Pat. No. 5,443,506

The patents discussed herein above are also incorporated by reference herein.

It should be understood that the above described embodiments constitute only examples of an accommodating lens assembly for implantation into the eye according to the present invention, and that the scope of the present invention fully encompasses other embodiments which may become obvious to those skilled in the art. For example, while implantation of the lens assembly in humans is described, the assembly may clearly also be applicable to other animals. Clearly, any and all possible permutations and/or combinations of different features as described above are within the scope of the present invention.

What is claimed is:

1. An implantable interfacial refraction ophthalmic lens assembly which adjusts its focal distance in response to changing physiologic needs of a user of said lens, the lens comprising a flexible optic chamber and cooperating haptics:

the optic chamber is defined by opposed, substantially parallel visually transparent circular discs, which are flexibly coupled at their edges and spaced apart to define a closed fluidic chamber, the fluidic chamber including first and second liquids, the liquids having different refractive indices and being immiscible so as to define a spherical or lenticular interface therebetween;

the haptics being coupled to the edge of the optic chamber and to the fluidic chamber so that application of force to the haptics deforms the fluidic chamber and changes the sphericity of the liquid interface;

whereby the focal length of the lens changes in response to application of force to the haptics in response to the changing physiologic need of the user to change the focal distance of the user of the lens without the need for movement of the lens assembly through its optical axis.

2. A lens according to claim 1 wherein the two liquids have substantially the same densities.

3. A lens according to claim 1 wherein the ophthalmic lens assembly is foldable.

4. An implantable interfacial refraction ophthalmic lens assembly which adjusts its focal distance in response to changing physiologic needs of the user of said lens, the lens comprising a flexible optic chamber and cooperating haptics:

the optic chamber is defined by opposed, substantially parallel visually transparent circular discs, which are flexibly coupled at their edges and spaced apart to define a closed fluidic chamber, the fluidic chamber including miscible first and second liquids having different refractive indices, the liquids being separated by an optically-acceptable membrane, the membrane being bonded to the circular disc edges so as to define a spherical or lenticular interface between the liquids;

the haptics being coupled to the edge of the optic chamber and to the fluidic chamber so that application of force to the haptics deforms the fluidic chamber and changes the sphericity of the liquid interface;

whereby the focal length of the lens changes in response to application of force to the haptics to change focus of the user.

5. A lens assembly according to claim 4 wherein the lens assembly is foldable.

6. A lens assembly according to claim 5 wherein the lens is adopted to be implantable into the eye using IOL injectors.

7. A lens assembly according to claim 4 wherein the difference between the refractive indices of the first and second liquids ($\Delta RI$) is at least about 0.1.

8. A lens assembly according to claim 4 wherein the difference between refractive indices ($\Delta RI$) is at least about 0.2.

9. An implantable interfacial refraction accommodating ophthalmic lens assembly which adjusts its focal distance in response to changing physiologic needs of the user of said lens, the lens comprising a flexible optic chamber and cooperating haptics:

the optic chamber is defined by opposed, substantially parallel visually transparent circular discs, which are flexibly coupled at their edges and spaced apart to define a closed fluidic chamber, the fluidic chamber including first and second liquids, the liquids having different refractive indices and being immiscible so as to define a spherical or lenticular interface therebetween;

the haptics being coupled to the edge of the optic chamber and to the fluidic chamber so that application of force to the haptics deforms the fluidic chamber and changes the sphericity of the liquid interface;

wherein the haptics define an internal chamber, the haptic chamber being in fluid communication with the optic chamber so that displacement of the haptics posteriorly permits fluid to flow into the optic chamber.

whereby the focal length of the lens changes in response to application of force to the haptics to change the focus of the user.

10. An ophthalmic lens according to claim 9 wherein the first and second liquids are separated by a visually transparent, elastic membrane.

11. An ophthalmic lens according to claim 9 wherein the membrane is attached to the edges of the circular discs which define the closed fluidic chamber so that the perimeter of the membrane separates, at least in part, the discs.

12. An ophthalmic lens according to claim 9 wherein the membrane has a varying thickness.

13. An ophthalmic lens according to claim 9 wherein the membrane is disposed between the circular discs.

* * * * *